US012245969B2

(12) United States Patent
Gueritee et al.

(10) Patent No.: US 12,245,969 B2
(45) Date of Patent: Mar. 11, 2025

(54) TEMPERATURE REGULATING SYSTEM

(71) Applicant: CLIM8, Tassin-la-Demi-Lune (FR)

(72) Inventors: Julien Gueritee, Eveux (FR); Florian Miguet, Venissieux (FR); Pierre Mouette, HK (CN)

(73) Assignee: CLIM8, Tassin-la-Demi-Lune (FR)

( * ) Notice: Subject to any disclaimer, the term of this patent is extended or adjusted under 35 U.S.C. 154(b) by 711 days.

(21) Appl. No.: 17/413,235

(22) PCT Filed: Dec. 14, 2018

(86) PCT No.: PCT/IB2018/001547
§ 371 (c)(1),
(2) Date: Jun. 11, 2021

(87) PCT Pub. No.: WO2020/121011
PCT Pub. Date: Jun. 18, 2020

(65) Prior Publication Data
US 2022/0031499 A1 Feb. 3, 2022

(51) Int. Cl.
*A61F 7/02* (2006.01)
*A61F 7/00* (2006.01)
(Continued)

(52) U.S. Cl.
CPC ............... *A61F 7/02* (2013.01); *G01K 1/14* (2013.01); *G01P 13/00* (2013.01); *G01P 15/18* (2013.01);
(Continued)

(58) Field of Classification Search
CPC ...... A61F 2007/0093; A61F 2007/0094; A61F 2007/0095; A61F 2007/0233;
(Continued)

(56) References Cited

U.S. PATENT DOCUMENTS 10,456,604 B2 * 10/2019 Cheatham, III .......... A61F 7/02
2017/0086513 A1    3/2017 Maxey et al.
2017/0265533 A1 *  9/2017 Gueritee ................ H05B 3/342

FOREIGN PATENT DOCUMENTS

DE        102015226237 A1    6/2017

OTHER PUBLICATIONS

International Search Report and Written Opinion issued for PCT/IB2018/001547.

* cited by examiner

Primary Examiner — Kaitlyn E Smith
(74) Attorney, Agent, or Firm — AEON Law, PLLC; Adam L. K. Philipp; Charlotte E. Holoubek

(57) ABSTRACT

A temperature regulation system for regulating the temperature of a portion of a body, in particular of a user's body. The system comprises one humidity sensor for measuring humidity in the vicinity of the portion of a body, one temperature adjustment element for providing heat to a portion of the body, a memory unit for storing one threshold humidity related value ($H_{thresh}$) and one reference user information related values ($t_{ref}$, $\theta_{ref}$), a controlling unit in communication with the humidity sensor, with the memory unit and with the temperature adjustment element, and configured to determine one instant user information related value ($t_{inst}$, $\theta_{inst}$), perform a comparison between one instant user information related value ($t_{inst}$, $\theta_{inst}$) and one triggering user information related value ($t_{trig}$, $\theta_{trig}$) based on said reference user information related value ($t_{ref}$, $\theta_{ref}$), activate the temperature adjustment element to provide heat to a portion of the body depending on the result of said comparison.

Figure 1:
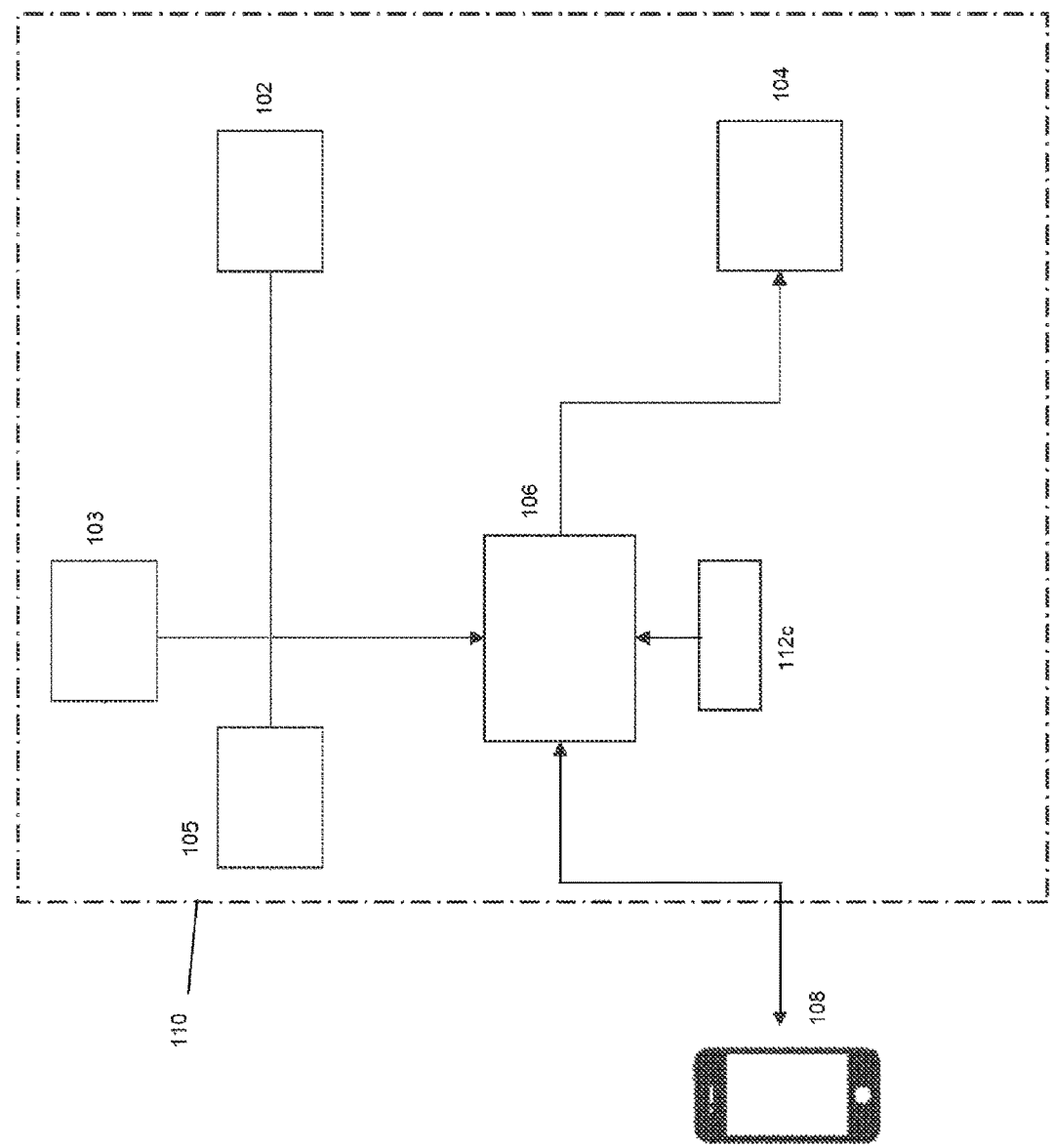

The controlling unit is further configured to receive one instant humidity ($H_{inst}$) measured in the vicinity of the portion of the body from the humidity sensor, perform a (Continued)

comparison between said instant humidity related value ($H_{inst}$) and one triggering humidity related value ($H_{trig}$) based on said threshold humidity related value ($H_{thresh}$), and to set the one triggering user information related value ($t_{trig}$, $\theta_{trig}$) to a value lower than said reference user information related value ($t_{ref}$, $\theta_{ref}$) when the instant humidity related value ($H_{inst}$) is greater or equal to said threshold humidity related value ($H_{thresh}$).

23 Claims, 2 Drawing Sheets

(51) Int. Cl.
*G01K 1/14* (2021.01)
*G01P 13/00* (2006.01)
*G01P 15/18* (2013.01)
*G16H 40/67* (2018.01)

(52) U.S. Cl.
CPC ...... G16H 40/67 (2018.01); *A61F 2007/0024* (2013.01); *A61F 2007/0025* (2013.01); *A61F 2007/0093* (2013.01); *A61F 2007/0234* (2013.01)

(58) Field of Classification Search
CPC ..... A61F 2007/0234; A61F 2007/0236; A41D 13/005; A41D 13/0051; A41D 13/0053
See application file for complete search history.

TEMPERATURE REGULATING SYSTEM

RELATED APPLICATIONS

This application is a U.S. national phase entry of and claims priority to PCT International Phase Application No. PCT/IB2018/001547, filed Dec. 14, 2018. The entire contents of the above-referenced applications and of all priority documents referenced in the Application Data Sheet filed herewith are hereby incorporated by reference for all purposes.

FIELD OF THE INVENTION

The present invention relates to a temperature regulation system for regulating the temperature of a portion of a body, in particular of a user's body.

BACKGROUND OF THE INVENTION

Thermal comfort is driven by the temperature inside a person's body and the temperature at the surface of the body. The deep body temperature of a person is generally 37° C., and the mean skin temperature of a person is generally 33° C. People become uncomfortable in a thermal sense when the environment changes, for example, increased wind or extra sunny day, or when a person moves to a cooler place. In common situations, discomfort in a thermal sense is felt by a user when the user's skin temperature changes, rather than a change in core body temperature.

Conventional chemical or electric heating systems used in clothing can easily deliver heat at relatively high levels. Most currently available devices consist of a wearable garments with heating pads that can be manually adjusted by the user. In at least some devices the heating pads produce an equal heat output and all the heating pads are activated to provide heat. Existing products are often bulky, heavy, require manual operation and are limited in their range of operation.

On top of this, these the efficiency of these systems also depends on the intensity of activity of the user, or on the humidity. Relative humidity around the body is an important determinant of thermal comfort, as thermal conductivity of water is much higher than that of air. As a consequence, heat will escape more easily from the body of the user when the water content in the air or in the clothing is high. So long as the user is physically active, this may not be an issue, as the heat produced by the muscle activity may be sufficient to compensate for the increase in heat transfer to the environment. However, when the user stops in the middle of, or at the end of an activity, the sweat accumulated on the skin, in the surrounding microclimate, and/or in the clothing itself may be causing cold discomfort.

SUMMARY OF THE INVENTION

The invention aims therefore at solving the problems mentioned above, amongst other problems.

To this end, the invention proposes a temperature regulated system that allows regulation of the temperature of a portion of a body based on humidity measured in the vicinity of the body.

According to a first aspect, the object of the invention is a temperature regulation system for regulating the temperature of a portion of a body, in particular of a user's body.

The system comprises:
at least one humidity sensor adapted to generate a humidity measurement that relates to humidity in the vicinity of the given portion of a body;
at least one temperature adjustment element adapted to provide heat to a given portion of the body;
a memory unit adapted to store at least one threshold humidity related value ($H_{thresh}$), and one or more reference user information related values ($t_{ref}$, $\theta_{ref}$);
a controlling unit in communication with the humidity sensor, with the memory unit and with the temperature adjustment element, and being configured to:
determine at least one instant user information related value ($t_{inst}$, $\theta_{inst}$);
perform a comparison between at least one instant user information related value ($t_{inst}$, $\theta_{inst}$) and at least one triggering user information related value ($t_{trig}$, $\theta_{trig}$), said at least one triggering user information related value ($t_{trig}$, $\theta_{trig}$) being based on one of said reference user information related values ($t_{ref}$, $\theta_{ref}$),
activate the temperature adjustment element to provide heat to a given portion of the body depending on the result of said comparison.

The controlling unit is further configured to receive at least one instant humidity ($H_{inst}$) measured in the vicinity of the given portion of the body from the humidity sensor, perform a comparison between said at least one instant humidity related value ($H_{inst}$) and at least one triggering humidity related value ($H_{trig}$), said at least one triggering humidity related value ($H_{trig}$) being based on said at least one threshold humidity related value ($H_{thresh}$), and to set the at least one triggering user information related value ($t_{trig}$, $\theta_{trig}$) to a value lower than the one of said reference user information related values ($t_{ref}$, $\theta_{ref}$) when the at least one instant humidity related value ($H_{inst}$) is greater or equal to said at least one threshold humidity related value ($H_{thresh}$).

In some embodiments, the system further comprises one or more of the following features, considered alone or according to any technically possible combination:
the humidity sensor is adapted to measure the level of water vapor in the air in the vicinity of the given portion of a body, and the at least one threshold humidity related value ($H_{thresh}$) is the threshold of water vapor saturation in the air in the vicinity of the given portion of a body;
the body is the body of a human or animal user, the humidity sensor being adapted to measurement next to, preferably in contact with, the skin of the given portion of the user body;
the system is adapted to be integrated in or on the inner or outer surface of a garment, said garment comprising at least one layer aimed at being preferably in contact with the user's skin, the humidity sensor being adapted to measurement in or on said layer;
the given portion of the body of the user is the back;
the given portion of the body of the user is a strip along, or around, the spine, preferably substantially 5 cm wide, and/or in an area between the two scapulae, and/or in an area in the lower region of the back;
at least one of the user information related values is the duration of a user inactivity period, the controlling unit being configured to determine instant duration of a user inactivity period based on a user activity information related to a user instant activity parameter, to activate the temperature adjustment element to provide heat to a given portion of the body when the at least one instant duration ($t_{inst}$) of a user inactivity period is greater or equal to the at least one triggering duration ($t_{trig}$), the controlling unit being further configured to set the at least one triggering duration ($t_{trig}$) to the at least one reference duration ($t_{ref}$) times Y, Y∈]0, 1[, preferably Y∈]0.4, 0.6[, most preferably Y being substantially equal to 0.5, when the at least one instant humidity related value ($H_{inst}$) is greater or equal to the at least one threshold humidity related value ($H_{thresh}$);

the user activity parameter is related to the activity of at least a portion of the body of the user, and the system further comprises at least one user activity sensor, adapted to generate a user activity measurement that relates to an activity of said at least a given portion of the body of the user, the controlling unit being in communication with the user activity sensor and being configured to receive the user activity measurement and to determine the user activity information from the user activity measurement;

the user activity parameter is related to the activity of at least a portion of the body of the user, and the system further comprises at least one user activity sensor, adapted to generate a user activity measurement that relates to an activity of said at least a given portion of the body of the user and to determine the user activity information from the user activity measurement, the controlling unit being in communication with the user activity sensor and being configured to receive the user activity information from the user activity sensor;

the user activity sensor is a motion sensor or a geographical position sensor, or a heartbeat sensor;

the user activity parameter is related to the activity of at least a portion of the body of the user, and the controlling unit comprises an interface adapted to receive from an external device a user activity measurement that relates to an activity of said at least a given portion of the body of the user, the controlling unit being configured to determine the user activity information from the user activity measurement;

the user activity parameter is related to the activity of at least a portion of the body of the user, and the controlling unit comprises an interface adapted to receive from an external device the user activity information.

wherein the user activity parameter is related to the activity of at least a portion of the body of the user, and the controlling unit comprises an interface adapted to receive as a manual input the user activity information;

at least one of the user activity parameters is related to the activity of at least a portion of the body of the user, and the controlling unit comprises an interface adapted to receive as a manual input a user activity measurement, the controlling unit being configured to determine the user activity information from the user activity measurement;

at least one of the user information related values is the temperature of a given portion of a user body, the system further comprising at least one temperature sensor adapted to generate a temperature measurement that relates to a temperature of a given portion of a body, the controlling unit being in communication with the temperature sensor, and being configured to receive the at least one instant temperature ($\theta_{inst}$) of a given portion of the body from the temperature sensor, activate the temperature adjustment element to provide heat to a given portion of the body when the at least one instant temperature related value ($\theta_{inst}$) is lower or equal to the at least one triggering temperature related value ($\theta_{trig}$), and set the at least one triggering temperature related value ($\theta_{trig}$) at the at least one reference temperature related value ($\theta_{ref}$) minus X ° C., X ∈]0, $\theta_{ref}$[, when the at least one instant humidity related value ($H_{inst}$) is greater or equal to the at least one threshold humidity related value ($H_{thresh}$);

the controlling unit is further configured to perform a comparison between the at least one instant temperature related value ($\theta_{inst}$) and at least one target temperature related value ($\theta_{targ}$), said at least one target temperature related value ($\theta_{targ}$) being based on the at least one reference temperature related value ($\theta_{ref}$), maintain the temperature adjustment element activated until the at least one instant temperature related value ($\theta_{inst}$) becomes equal to said at least one target temperature related value ($\theta_{targ}$), and set said at least one target temperature related value ($\theta_{targ}$) to a value greater than said at least one reference temperature related value ($\theta_{ref}$) when the at least one instant humidity related value ($H_{inst}$) is greater or equal to the at least one threshold humidity related value ($H_{thresh}$);

the controlling unit is configured to communicate wirelessly with an external device;

the system comprises a power supply for supplying power to the controlling unit and the logical unit;

the power supply is an external power supply;

According to a second aspect, the object of the invention is also a garment to be worn by a human or animal user comprising a temperature regulation system as presented above.

Such a temperature regulating system, and such garment integrating said temperature regulating system, as presented above, allow a finer automatic adjustment of the temperature depending on the humidity in the vicinity of a portion of the user's body and/or in the garment, and taking into account a user related information such as the user activity (or non-activity) and/or the temperature of a portion of the user's body.

DRAWINGS

Figure 2:
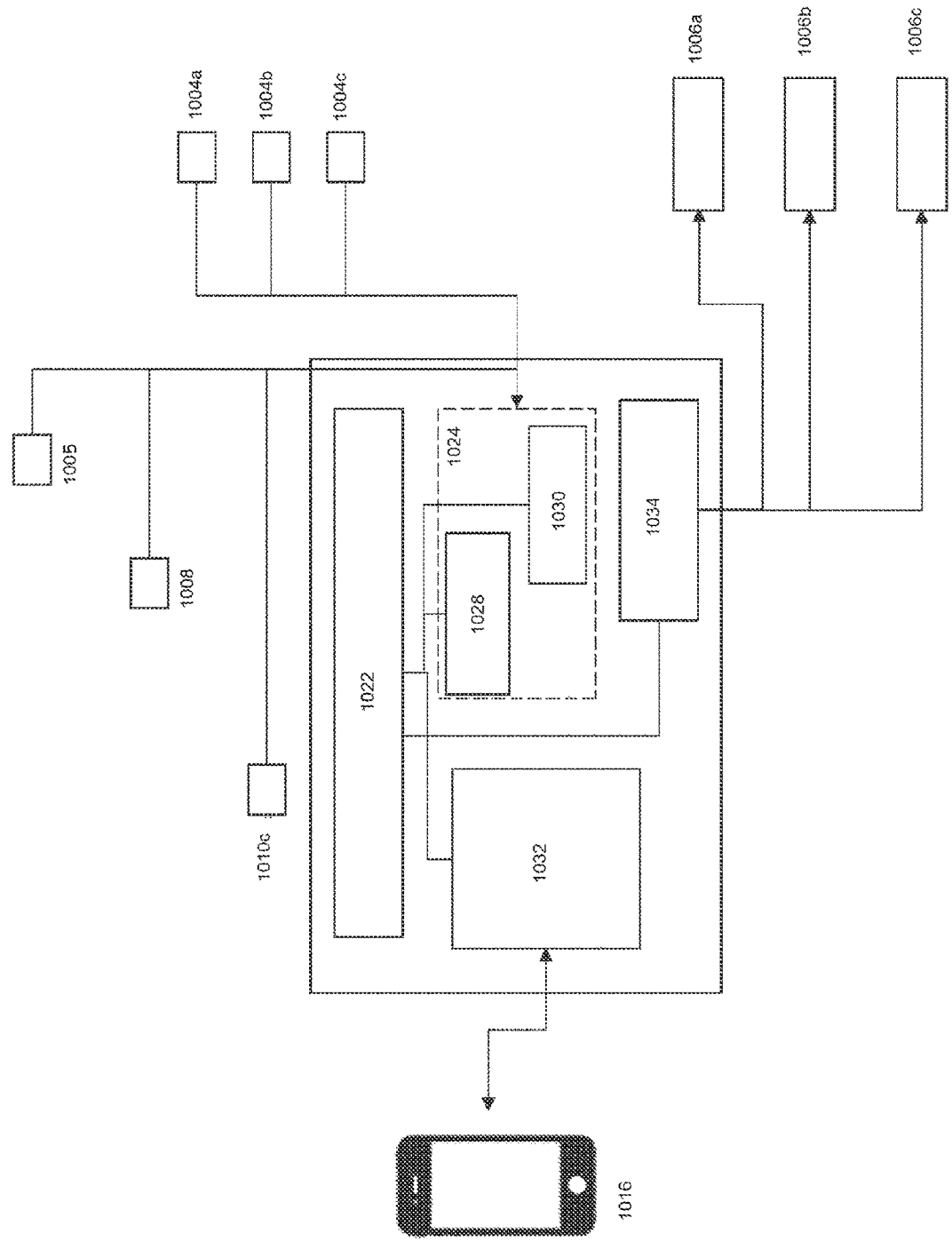

The invention and its advantages may be better understood by referring to the description which follows, given as example and for illustrative purpose only, and by referring to the accompanying drawings listed below:

FIG. 1: shows a generalized temperature regulation system;

FIG. 2: shows a schematic diagram of a controller that can be used in the temperature regulation system shown in FIG. 1.

DETAILED DESCRIPTION

FIG. 1 shows a schematic of a generalized temperature regulation system. As shown in FIG. 1, the temperature regulation system 100 comprises at least one humidity sensor 103, at least one temperature adjusting element 104, such as a heating element, a controlling unit or controller 106 and a user device 108.

The humidity sensor 103 is not necessarily located close to the temperature adjusting element 104.

The system may further comprise a flexible support 110 that can be a wearable article 110, or that can be integrated in such a wearable article, such as a garment.

As shown in FIG. 1, the humidity sensor 103 is disposed on the flexible support 110, such that it can measure the humidity in the vicinity of a portion of the user's body.

The flexible support 110 can be, or integrated in, any suitable garment 110 that a user can wear on a portion of the user's body. For example, the garment 110 can be a long sleeve shirt, T-shirt, hat, socks, gloves, pants, tights, jacket, beanie or any other suitable wearable garment.

In a specific embodiment, at least one temperature sensor 102 is disposed on the flexible support 110 such that the temperature sensor 102 is in contact with a portion of the user's body. The temperature sensor 102 is at least directly in contact with the user's skin. Alternatively, the temperature sensor 102 is indirectly in contact with the user's skin, for example through a layer of the garment. The sensor 102 is configured to measure the skin temperature of the user.

The temperature sensor 102 is configured to generate a temperature measurement that corresponds to the temperature at a portion of the user's body. Preferably the temperature measurement is a skin temperature.

The temperature adjusting element 104 can be any suitable element or device to provide heat or cold to a user. For example, the temperature adjusting element 104 may be a heating pad that can be positioned on the wearable garment 110 and arranged in direct contact with the user's skin or in contact through a layer of textile, to provide heat to a portion of the user's body. The temperature adjusting element 104 provides heat to increase the skin temperature of the user. Alternatively, the temperature adjusting element can be an air conditioning unit in a car or home or can be a smart appliance or a HVAC system of a building or any other suitable device or system to provide heat or cold to a user.

The controller 106 is configured to receive the humidity related measurement from the humidity sensor 103, and, when a temperature sensor 102 is used, the temperature related measurement from this temperature sensor 102. The controller 106 is in wire or wireless communication with the humidity sensor 103, the temperature adjusting element 104, and when applicable with the temperature sensor 102. The controller 106 receives the humidity related measurement from the humidity sensor 103, and when applicable the temperature measurement from the temperature sensor 102, as electronic signals. The controller 106 is configured to process these signals and/or to receive already signals already processed for example by the sensors themselves.

The system comprises further a memory unit 101 adapted to store at least one threshold humidity related value $H_{thresh}$. The controller 106 is also in communication with the memory unit 101.

The controller 106 is configured to receive an instant humidity related value $H_{inst}$, related to the humidity in the vicinity of a given portion of the body, from the humidity sensor 103, this value being measured in the vicinity of the given portion of the body, and to receive, when applicable, the instant temperature $\theta_{inst}$ of a given portion of the body from the temperature sensor 102.

Besides, as will be explained in examples further below, the controller 106 if configured to determine at least one instant user information related value, that can be for example an instant temperature $\theta_{inst}$ of a given portion of the body, or an instant duration $t_{inst}$ of a user inactivity period.

The controller 106 is configured to perform a comparison between at least one instant user information related value $t_{trig}$, $\theta_{inst}$, and at least one triggering user information related value $t_{trig}$, $\theta_{trig}$, such as a triggering user inactivity period duration value $t_{trig}$ or a triggering temperature related value $\theta_{trig}$, and activate the temperature adjustment element 104 to provide heat or cold to a given portion of the body depending on the result of the comparison.

The triggering user information related value $t_{trig}$, $\theta_{trig}$ is based on one reference user information related values $t_{ref}$, $\theta_{ref}$ also stored in the memory unit 101, such as a reference user inactivity period duration value $t_{ref}$ or a reference temperature related value $\theta_{ref}$.

In some specific embodiment, the memory unit 101 may also be adapted to store at least one user profile information related to a user profile parameter.

The controller 106 is further configured to perform a comparison between the instant humidity related value $H_{inst}$ and at one triggering humidity related value $H_{trig}$. This triggering humidity related value $H_{trig}$ is based on the threshold humidity related value $H_{thresh}$. The controller 106 is also configured to set the triggering user information related value $t_{trig}$, $\theta_{trig}$ to a value lower than the reference user information related value $t_{ref}$, $\theta_{ref}$ when the instant humidity related value $H_{inst}$ is greater or equal to the threshold humidity related value $H_{thresh}$.

Many humidity sensors exist, with variation in terms of sensing precision and size.

Preferably, the humidity sensor 103 should be small enough to be able to detect humidity at the level of the base layer of a garment in which the system is integrated, next to the skin, and yet not impairing the movements of the wearer, the fit, nor increasing the bulkiness of the clothing ensemble.

The humidity sensor 103 measures humidity and send the information to the controller 106 continuously or regularly, as frequently as possible. The threshold humidity related value $H_{thresh}$ can be predefined in the memory unit 101, and should be as low as possible, but it can also be determined during a calibration process and then stored in the memory unit 101.

As an example, the humidity sensor 103 can be a sensor adapted to measure the level of water vapor in the air in the vicinity of the given portion of a body. In such a case, the threshold humidity related value $H_{thresh}$ is the threshold of water vapor saturation in the air in the vicinity of the given portion of a body, this threshold of water vapor saturation in the air being, by definition, dependent on the temperature.

The invention can apply for example to a human user or animal user, the body being then the body of the human or animal user. In such cases, the humidity sensor 103 is adapted to measurement next to the skin of the corresponding portion of the user body, preferably in contact with the skin.

As mentioned above, the system is particularly adapted to be integrated in a garment. The system is then more precisely adapted to be integrated in or on the inner or outer surface of such a garment.

The garment comprises at least one layer. This layer is preferably aimed at being in contact with the user's skin, and the humidity sensor 103, and when applicable also the temperature sensor 102, are adapted to measurement in or on said layer.

The body portion in question can be the user's back. More particularly, it can be a strip along, or around, the spine, preferably substantially 5 cm wide. It can also be an area between the two scapulae, or an area in the lower region of the back. By using more than one humidity sensors, and when applicable temperature sensors, more than one body portion can be addressed by a system according to the invention.

In one embodiment according to the invention, one way of taking account of the humidity factor to regulate the temperature of a portion of a body, is to use a user inactivity period as the user information related value, to adjust the duration of an inactivity period after which the temperature adjustment is activated.

In normal conditions, the controller 106 is configured to activate the temperature adjustment element after an inactivity period which lasts more than a triggering duration $t_{trig}$, the latter being dependent on a reference duration $t_{ref}$ stored in the memory unit 101. It means that the controller 106 is configured to determine the instant duration $t_{inst}$ of a user inactivity period, based on a user activity information related to a user instant activity parameter, to activate the temperature adjustment element 104, when the this instant duration $t_{inst}$ is greater or equal to the triggering duration $t_{trig}$.

In said normal conditions, meaning normal humidity conditions, the controller 106 may be configured for example such that this triggering duration $t_{trig}$ is equal to the reference duration $t_{ref}$.

In this embodiment, to account of the humidity factor, the controller 106 is further configured to set this triggering duration $t_{trig}$ to $t_{ref} \times Y$, where Y is a number strictly greater than 0 and strictly smaller than 1, when the humidity exceeds a threshold value. In an example, this means when the instant humidity related value $H_{inst}$ measured by the humidity sensor 103 is greater or equal to the threshold humidity related value $H_{thresh}$.

Preferably, the controller 106 can be configured such that Y is strictly greater than 0.4 and strictly slower than 0.6, substantially equal to 0.5.

The value for Y can vary, depending on the type of activity, the intensity of the activity, the season, the time in the day, the user profile, etc. . . . It can be setup when the system is built and/or can be modified at anytime by the user through an appropriate interface on an external device or apparatus, or one the user device 108 itself.

The user activity parameter is related to the activity of at least a portion of the body of the user, and the system also comprises at least one user activity sensor, not shown on the figures. This user activity sensor is adapted to generate a user activity measurement that relates to an activity of the given portion of the body of the user.

The controller 106 is in communication with the user activity sensor and is configured to receive the user activity measurement and to determine the user activity information from the user activity measurement.

Alternatively, the user activity sensor is also adapted to determine the user activity information from the user activity measurement. In that case, the controller 106, in communication with the user activity sensor, is configured to receive directly the user activity information from the user activity sensor.

The user activity sensor may be a motion sensor, or a geographical position sensor, or a heartbeat sensor. The system may comprise several activity sensors, each being for example of one of the type mentioned above.

In the case of a motion sensor, this sensor can be a 3-axis accelerometer. The accelerometer detects or measures the body movements of the user. The motion measurement is an acceleration measurement or a velocity measurement. The motion measurement is sampled by the controller 106 from the motion sensor. The motion sensor is sampled at any suitable sampling rate. The controller 106 uses the motion measurement to adjust the threshold temperature based on a predetermined relationship.

The controller 106 may comprises an interface adapted to receive from an external device the user activity measurement. The controller 106 is then configured to determine the user activity information from the user activity measurement received via said interface.

Alternatively, the interface is adapted to receive from an external device directly the user activity information.

The interface may also be adapted to receive the user activity information as a manual input from a user.

Alternatively, the interface is adapted to receive a user activity measurement as a manual input. Then, the controller 106 is configured to determine the user activity information from the user activity measurement received via the interface.

In another embodiment according to the invention, another way of taking account of the humidity factor to regulate the temperature of a portion of a body, is to use the temperature of a portion of the body of the user as the user information related value, to adjust temperature that triggers the activation of the temperature adjustment element 104.

In normal conditions, the controller 106 is configured to activate the temperature adjustment element when the instant temperature related value $\theta_{inst}$ falls below the triggering temperature related value $\theta_{trig}$, the latter being dependent on the reference temperature related value $\theta_{ref}$ stored in the memory unit 101.

In that specific embodiment, the system further comprises the temperature sensor 102, already mentioned above. This temperature sensor 102 is adapted to generate a temperature measurement that relates to a temperature of a given portion of the body. The controller 106 is in communication with the temperature sensor 102 and is configured to receive the instant temperature $\theta_{inst}$ of the given portion of the body from the temperature sensor 102, activate the temperature adjustment element 104 to provide heat to this portion of the body when the instant temperature related value $\theta_{ref}$ is lower or equal to the triggering related value $\theta_{trig}$.

In said normal conditions, meaning normal humidity conditions, the controller 106 may be configured for example such that this triggering temperature related value $\theta_{trig}$ is equal to the reference temperature related value $\theta_{ref}$.

In this embodiment, to account of the humidity factor, the controller 106 is further configured to set this triggering temperature related value $\theta_{trig}$ such that $\theta_{trig} = \theta_{ref} - X$, with X being a number strictly greater than 0 and strictly smaller than $\theta_{ref}$, when the humidity exceeds a threshold value. In an example, this means when the instant humidity related value $H_{inst}$ measured by the humidity sensor 103 is greater or equal to the threshold humidity related value $H_{thresh}$.

The controller 106 can also be further configured to perform the following steps:
- comparison between the instant temperature related value $\theta_{inst}$ received from the temperature sensor 102, and one target temperature related value $\theta_{targ}$, with this target temperature related value $\theta_{targ}$ being also based on the reference temperature related value $\theta_{ref}$;
- maintaining the temperature adjustment element 104 activated until the instant temperature related value $\theta_{inst}$ continuously or regularly received from the temperature sensor 102; becomes equal to the target temperature related value $\theta_{targ}$;
- set the target temperature related value $\theta_{targ}$ to a value greater than the reference temperature related value $\theta_{ref}$ when the instant humidity related value $H_{inst}$ is greater or equal to the threshold humidity related value $H_{thresh}$.

The user device 108 is a portable device that includes at least a processor, a memory and a user interface, that can be used by the user as an input-output interface. The user device 108 is a low energy wireless system. The user device 108 may, for example, be a smartphone or a tablet. The user device 108 is adapted for two-way communication with the controller 106, such that information can be transmitted from the user device 108 to the controller 106 and information can be transmitted from the controller 106 to the user device 108. The user device 108 preferably uses a low energy wireless system such as Bluetooth or infra-red as the wireless communication protocol.

The system 100 further comprises a power source 112c that is connected to the controller 106 to power the controller 106. The power source 112c can transmit power via a wired connection or wirelessly. The controller 106 and the power source 112c are preferably disposed on the wearable garment 110.

Alternatively, the power source can be the power source of the user device 108.

The controller 106 includes at least a processor, a memory unit and a power unit. The power unit generates power and the power unit preferably comprises rechargeable batteries. The processor, memory unit and power unit are preferably arranged in a casing.

The structure and operation of the controller for the temperature regulation system will now be described with respect to FIG. 2, which shows a controller 1000. The controller 106 has a structure that is the same as controller 1000 described with respect to FIG. 2, and functions like this controller 1000.

FIG. 2 shows a generalized schematic of the controller 1000 in communication with humidity sensors 1008, a plurality of temperature adjusting elements 1006a-1006c, and at least one user activity sensor such as a motion sensor 1010c. It comprises also, in one embodiment described above, one or more temperature sensors 1004a-1004c. The sensors shown in FIG. 2 are generic representations to illustrate operation of the generalized controller 1000. The functionality of the controller and interaction with the sensors and user device is applicable in any of the earlier embodiments described.

As shown in FIG. 2, controller 1000 comprises a logical unit 1022, such as a processor 1022, a memory unit 1024 and a power unit 1026. The controller 1000, in this example, is a microcontroller, i.e. it includes all components on a single chip or integrated circuit. The processor 1022 is a microprocessor that can process electronic commands. The processor 1022 can execute commands stored in the non-transitory computer readable memory unit 1024. The processor 1022 is preferably in the form of an integrated circuit. The memory unit 1024 comprises ROM 1028 and RAM 1030. The power unit 1026 includes one or more rechargeable batteries that are disposed in a casing and in communication with the processor. The controller 1000 also includes other essential electronic components for interfacing the various components described and appropriate interfacing circuitry.

The controller 1000 further includes a communication module 1032 which is functionally part of a controlling unit 1032, 1034. The communication module 1032 is low energy wireless system such as a Bluetooth module. The communication module 1032 is in wire or wireless communication with the processor 1022 and allows the controller 1000 to communicate with a user device 1016.

A local application that is executable on the user device 1016 allows communication between the user device 1016 and the controller. The application also allows for a user to access an interface that allows a user to input for example user profile information (as described earlier) as well as additionally modify controller operating modes.

The controller 1000 is also in communication with the plurality of humidity sensors, and when applicable temperature sensors, and temperature adjusting elements that are disposed for example on a wearable garment, and is configured as explained above with respect of FIG. 1

The controller 1000 is also configured to deactivates the temperature adjusting element after a certain amount of time and/or once the instant temperature measurement exceeds the threshold temperature. It should be noted that the temperature sensors described herein measure the skin temperature, but alternative sensors can be used that allow other temperature measurements such as muscle temperature or core temperature and so on.

Each humidity sensor, and when applicable temperature sensor, can be associated with a temperature adjusting element. The controller 1000 receives a plurality of measurements from each of the sensors, and uses each of these measurements as explained above relatively to a configuration with one humidity sensor, when applicable one temperature sensor, and one temperature adjusting element. The controller 1000 allows thus for localized or selective temperature adjustment of specific portions of the user's body.

The controller 1000 is configured to provide an activation signal along the power lines to the temperature adjusting elements 1006a-1006c. The activation signal is preferably a pulse width modulated (PWM) power signal. The controller 1000 includes a PWM module 1034 which is functionally part of the controlling unit 1032, 1034. This PWM module 1034 can be integrated into the processor or connected to the processor and the power unit. The PWM module 1034 generates a PWM signal and transmits such along the power lines to the heating pads 1006a-1006c. A PWM signal conserves the power from the power unit.

The temperature regulation system as described is advantageous because the system regulates a temperature distribution across a user's skin and selectively energizes or activates a temperature adjusting element in the corresponding location. Further the temperature regulation system as described is also advantageous because the system takes into account humidity that can affect a person's thermal comfort or sense of comfort.

It is to be reminded that the two main specific embodiments described above can be combined in a single regulation system according to the invention.

The humidity becomes particularly a problem when the user is inactive. In an inactive state, the user produces less heat, and humidity (water) evaporates, leading to a cooling of the garment microclimate, possibly the skin itself. On top of this, when the garment microclimate is saturated in water, the body heat loss towards the environment is faster.

This is why the regulation system of the invention is of particular importance, to account of the humidity factor to regulate the temperature of a portion of the user body.

In one of the embodiments described above, when the instant humidity related value goes over the threshold humidity related value, such as the threshold of water vapor saturation in the air in the vicinity of the body portion in question, the delay before activating the temperature adjustment element during a pause of activity, or inactivity period, is reduced, for example is divided by two.

For example, when the user runs during 10 minutes in the cold, the temperature adjustment element is activated during the first 5 minutes of running, and then is deactivated. At the $11^{th}$ minutes, thus after 1 minute of pause in conditions of low humidity, the temperature adjustment element would be activated again. But in order to take into account the increase of humidity during the run, the system will activate the temperature adjustment element after 30 seconds only, instead of 1 minute.

Also, when the user is static or quasi-static, in the cold, and in an environment where humidity is increasing, or is higher than at the time of calibration (initial configuration of the system), and even if the temperature is stable, the system will account of this specific configuration by activating the temperature adjustment element when the instant temperature related value reach a value lower than the reference temperature related value which could be otherwise used for triggering the activation.

The above description has been directed to specific embodiments of this invention which is, however, not limited to these embodiments described for purpose of example only.

In particular, the invention concerns not only a temperature regulation system for regulating the temperature of a portion of a human or animal user's body, but more generally the for regulating the temperature of a portion of a any other body such as a recipient for receiving food or a liquid.

Besides, the above description relates to a controller, comprising a logical unit, a memory unit and controlling unit, in communication with the temperature sensors, the heat adjustment elements, and the user device. Alternatively, the memory unit may be part of one of the temperature sensors or of the user device, and the logical unit may be part of the user device.

Also, the above description relates to examples where the system is integrated to a wearable garment for a user, human or animal. But it extends to a system integrated or part of an accessory such as a belt, a wrist lace or a watch, a shoe, etc. . . .

The invention claimed is:

1. A temperature regulation system for regulating the temperature of a body, the temperature regulation system comprising:
   at least one humidity sensor adapted to generate a humidity measurement that relates to humidity in the vicinity of a given portion of a body;
   at least one temperature adjustment element adapted to provide heat to a given portion of the body;
   a memory unit adapted to store at least one threshold humidity related value, and one or more reference user information related values, said reference user information related value being a reference duration of a user inactivity period;
   a controlling unit in communication with the humidity sensor, with the memory unit and with the temperature adjustment element, and being configured to:
      determine at least one instant duration of a user inactivity period based on a user activity information related to a user instant activity parameter, the controlling unit being further configured to determine or receive said user activity information;
      perform a comparison between at least one instant duration of a user inactivity period, and at least one triggering duration of a user inactivity period, said at least one triggering duration of a user inactivity period being based on one of said reference duration of a user inactivity period,
      activate the temperature adjustment element to provide heat to a given portion of the body when the at least one instant duration of a user inactivity period is greater or equal to the at least one triggering duration,
      receive at least one instant humidity related value measured in the vicinity of the given portion of the body from the humidity sensor, perform a comparison between said at least one instant humidity related value and at least one triggering humidity related value, said at least one triggering humidity related value being based on said at least one threshold humidity related value, and to set the at least one triggering duration of a user inactivity period to a value lower than the one of said reference duration of a user inactivity period when the at least one instant humidity related value is greater or equal to said at least one threshold humidity related value, by setting the at least one triggering duration of a user inactivity period to the at least one reference duration times Y, Y∈]0,1[.

2. The temperature regulation system of claim 1, wherein the humidity sensor is adapted to measure the level of water vapor in the air in the vicinity of the given portion of a body, and the at least one threshold humidity related value is the threshold of water vapor saturation in the air in the vicinity of the given portion of a body.

3. The temperature regulation system of claim 1, wherein the body is the body of a human or animal user, the humidity sensor being adapted to measurement next to, or in contact with, the skin of the given portion of the user body.

4. The temperature regulation system of claim 3, wherein the system is adapted to be integrated in or on the inner or outer surface of a garment, said garment comprising at least one layer aimed at being next to, or in contact with, the user's skin, the humidity sensor being adapted to measurement in or on said layer.

5. The temperature regulation system of 3, wherein the given portion of the body of the user is the back.

6. The temperature regulation system of claim 5, wherein the given portion of the body of the user is a strip along, or around, the spine, or in an area between the two scapulae, or in an area in the lower region of the back, or any combination of said strip, said area between the two scapulae and said area in the lower region of the back.

7. The temperature regulation system of claim 6, wherein the strip is substantially 5 cm wide.

8. A temperature regulation system of claim 1, wherein, Y∈]0.4, 0.6[.

9. The temperature regulation system of claim 8, wherein the user activity parameter is related to the activity of at least a portion of the body of the user, and the system further comprises at least one user activity sensor, adapted to generate a user activity measurement that relates to an activity of said at least a given portion of the body of the user, the controlling unit being in communication with the user activity sensor and being configured to receive the user activity measurement and to determine the user activity information from the user activity measurement.

10. The temperature regulation system of claim 9, wherein the user activity sensor is a motion sensor or a geographical position sensor, or a heartbeat sensor.

11. The temperature regulation system of claim 8, wherein the user activity parameter is related to the activity of at least a portion of the body of the user, and the system further comprises at least one user activity sensor, adapted to generate a user activity measurement that relates to an activity of said at least a given portion of the body of the user and to determine the user activity information from the user activity measurement, the controlling unit being in communication with the user activity sensor and being configured to receive the user activity information from the user activity sensor.

12. The temperature regulation system of claim 11, wherein the user activity sensor is a motion sensor or a geographical position sensor, or a heartbeat sensor.

13. The temperature regulation system of claim 8, wherein the user activity parameter is related to the activity of at least a portion of the body of the user, and the controlling unit comprises an interface adapted to receive from an external device a user activity measurement that relates to an activity of said at least a given portion of the body of the user, the controlling unit being configured to determine the user activity information from the user activity measurement.

14. The temperature regulation system of claim 8, wherein the user activity parameter is related to the activity of at least a portion of the body of the user, and the controlling unit comprises an interface adapted to receive from an external device the user activity information.

15. The temperature regulation system of claim 8, wherein the user activity parameter is related to the activity of at least a portion of the body of the user, and the controlling unit comprises an interface adapted to receive as a manual input the user activity information.

16. The temperature regulation system of claim 8, wherein at least one of the user activity parameter is related to the activity of at least a portion of the body of the user, and the controlling unit comprises an interface adapted to receive as a manual input a user activity measurement, the controlling unit being configured to determine the user activity information from the user activity measurement.

17. The temperature regulation system of claim 8, wherein Y substantially equal to 0.5.

18. The temperature regulation system of claim 1, wherein at least one of the user information related values being a temperature of a given portion of a user's body, the system further comprising at least one temperature sensor adapted to generate a temperature measurement that relates to the temperature of a given portion of a user's body, the controlling unit being in communication with the temperature sensor, and being configured to receive the at least one instant temperature of a given portion of the body from the temperature sensor, activate the temperature adjustment element to provide heat to a given portion of the body when the at least one instant temperature related value is lower or equal to the at least one triggering temperature related value, and set the at least one triggering temperature related value at the at least one reference temperature related value minus X° C., X∈]0, $\theta_{ref}$[, when the at least one instant humidity related value is greater or equal to the at least one threshold humidity related value.

19. The temperature regulation system of claim 18, wherein the controlling unit is further configured to perform a comparison between the at least one instant temperature related value and at least one target temperature related value, said at least one target temperature related value being based on the at least one reference temperature related value, maintain the temperature adjustment element activated until the at least one instant temperature related value becomes equal to said at least one target temperature related value, and set said at least one target temperature related value to a value greater than said at least one reference temperature related value when the at least one instant humidity related value is greater or equal to the at least one threshold humidity related value.

20. The temperature regulation system of claim 1, wherein the controlling unit is configured to communicate wirelessly with an external device.

21. The temperature regulation system of claim 1, further comprising a power supply for supplying power to the controlling unit.

22. The temperature regulation system of claim 21, wherein the power supply is an external power supply.

23. A garment to be worn by a human or animal user comprising a temperature regulation system claim 1.

* * * * *